(12) United States Patent
    Tata

(10) Patent No.: US 9,857,342 B2
(45) Date of Patent: Jan. 2, 2018

(54) DEVICE TO ADJUST GAS CONCENTRATION IN FLUIDS

(71) Applicant: Murthy Tata, Chandler, AZ (US)

(72) Inventor: Murthy Tata, Chandler, AZ (US)

(73) Assignee: Murthy Tata, Chandler, AZ (US)

( * ) Notice: Subject to any disclaimer, the term of this patent is extended or adjusted under 35 U.S.C. 154(b) by 291 days.

(21) Appl. No.: 14/933,067

(22) Filed: Nov. 5, 2015

(65) Prior Publication Data

US 2016/0054278 A1    Feb. 25, 2016

Related U.S. Application Data

(62) Division of application No. 13/691,403, filed on Nov. 30, 2012, now Pat. No. 9,207,222.

(Continued)

(51) Int. Cl.
    *G01N 33/00*    (2006.01)
    *G01N 33/14*    (2006.01)
    (Continued)

(52) U.S. Cl.
    CPC ............ *G01N 33/0006* (2013.01); *A23L 2/54* (2013.01); *C12G 1/06* (2013.01); *C12G 3/00* (2013.01); *G01N 33/14* (2013.01)

(58) Field of Classification Search
    CPC ...... G01N 33/0006; G01N 33/14; A23L 2/54; C12G 1/06; C12G 3/00
    See application file for complete search history.

(56) References Cited

U.S. PATENT DOCUMENTS 6,848,258 B1 *    2/2005  Speece .................. B01F 3/0446
                                                   60/649
9,207,222 B2 *   12/2015  Tata .................... G01N 33/0006
                        (Continued)

*Primary Examiner* — Anthony Weier

(57) ABSTRACT

A device to adjust concentration of a first gas in a fluid to a target concentration ($C_f$) is provided. The device includes a container, having a first opening, the container is configured to receive a first volume ($V_L$) of the fluid through the first opening. Wherein the fluid has an initial concentration ($C_i$) of the first gas and a second volume ($V_C$) of the container is determined based on the initial concentration ($C_i$) of the first gas in the fluid, a target concentration ($C_f$) of the first gas in the fluid, a partition coefficient ($\varphi$) of the first gas, and the first volume ($V_L$), and configured to adjust pressure in the container at a predetermined pressure of the first gas to adjust the first gas concentration in the fluid to the target concentration ($C_f$); wherein the second volume ($V_C$) and the first volume ($V_L$) are correlated by:

$$\frac{V_C}{V_L} = \frac{1}{\Phi}\left[\frac{M}{C_f V_L} + \frac{C_i}{C_f} - 1\right] + 1$$

in that M is an amount of the first gas required to be introduced in the container to adjust the first gas concentration in the fluid to the target concentration ($C_f$).

20 Claims, 4 Drawing Sheets

Related U.S. Application Data

(60) Provisional application No. 61/629,996, filed on Dec. 2, 2011.

(51) Int. Cl.
*A23L 2/54* (2006.01)
*C12G 1/06* (2006.01)
*C12G 3/00* (2006.01)

(56) References Cited

U.S. PATENT DOCUMENTS

2011/0070331 A1* 3/2011 Watson ............... C12G 3/065
　　　　　　　　　　　　　　　　　426/15
2013/0256924 A1* 10/2013 Osaki ............... B01F 3/04737
　　　　　　　　　　　　　　　　　261/27

* cited by examiner

US 9,857,342 B2

DEVICE TO ADJUST GAS CONCENTRATION IN FLUIDS

CROSS-REFERENCE TO THE RELATED APPLICATION(S)

The underlying concepts, but not necessarily the language, of the U.S. provisional application No. 61/629,996 filed on Dec. 2, 2011—from which this application claims benefit of priority- and the U.S. patent application Ser. No. 13/691,403 filed on Nov. 30, 2012—which has now been accepted by the US Patent Office, now U.S. Pat. No. 9,207,222, and of which this application is a divisional application—are incorporated in this application by reference. Both the above referred patent applications bearing Ser. No. 61/629,996 and Ser. No. 13/691,403 and contents as disclosed therein are made part of this application and are treated as if disclosed in their entirety in this application.

TECHNICAL FIELD

The present subject matter relates to a device to adjust gas concentration in a fluid. More particularly, the device relates to adjusting gas concentration in beverages.

BACKGROUND

Dissolved gases play an important role in defining the character of various beverages and foods. For example, carbonated beverages such as sodas and beer require that a defined amount of carbon dioxide gas be dissolved in the beverage. The texture and porosity of baked goods and leavened breads is usually created by carbon dioxide that is produced either by yeast or bicarbonate salts during the proofing and baking processes. It is critically important that the proper concentrations of dissolved gases are maintained in the products to maintain consistent product characteristics such as appearance, taste, mouthfeel and flavor perception.

Maintaining concentration of gases in fluids at the point of service poses a significant problem because during product distribution and shelf storage, changes in temperature can alter the solubility of gas in the product. In certain cases where more than one gas species is present in the fluid, changes in temperature and other physical parameters during storage and distribution can prove disastrous for product quality. For example, with certain beers, besides carbon dioxide, a certain amount of nitrogen is added to the beer to modify its character. Nitrogen produces very fine bubbles in the beer that create a tight, long-lasting head of foam and a distinct mouthfeel that is often described as "creamy". While the breweries may produce precisely controlled packages, maintaining the proper composition of the respective dissolved gases in such beers is extremely difficult once the product leaves the brewery. Owing to the different solubility parameters of nitrogen and carbon dioxide in beer, any change physical parameters such as temperature, pressure etc. results in adversely affecting the beer quality. Or in case of keg beer, in addition to the temperature pressure and composition of the counter pressure gas or a dispense gas can adversely affect beer quality.

Maintaining the proper dissolved gas composition in products at the time of dispense has been especially challenging for the beverage industry. The present subject matter provides a solution for the above and other problems.

SUMMARY

For the purpose of illustration, following discussion uses beer and water as example fluids to explain the present subject matter. However, it would be understood that the present subject matter may be practiced with other fluids, including but not limited to products such as coffees, smoothies, milkshakes, batters, doughs, as well as other edible or non-edible fluids without departing from the spirit of the present subject matter.

Presently, breweries package beer with a precise level of dissolved carbon dioxide. The dissolved gas levels are often tightly controlled to within 10% of the desired target concentration. It is sometimes of interest to the consumer to change the dissolved gas level in the beer from the levels packaged at the brewery. For example, reducing carbonation level will allow for a smoother taste perception without the carbonation "bite". At present, there is no reliable way to adjust the carbonation level to a value different from what the brewery provided, prior to serving. Likewise, there is no reliable way for to increase the carbonation level to a value greater than provided by the brewery. The present subject matter offers a way to conveniently adjust gas concentration in beverages prior to serving.

The challenge is even greater in the case of nitrogenated beers. Nitrogenated beers are produced at the brewery by incorporating a defined amount of nitrogen in addition to carbon dioxide into the beer. Since nitrogen is only sparingly soluble in beer, any changes in storage temperature can cause substantial amounts of nitrogen to strip out of the beer, never to return to beer during normal handling. Likewise, keg beer containing nitrogen requires a mixture of nitrogen and carbon dioxide gases to counter-pressure the kegs. Any variation in gas composition or magnitude of the counter-pressure gas, or the temperature cause significant deterioration in product quality at the point of service.

In addition to other solution, the present subject matter also provides a solution to convert a normally carbonated beer into a nitrogenated beer style. Accomplishing this style conversion requires removing a defined amount of carbon dioxide from the beer and adding a defined amount of nitrogen.

According to one aspect, the present subject matter provides a device to adjust concentration of a first gas in a fluid to a target concentration ($C_f$) comprising: a container, the container comprises a first opening, the container is configured to receive a first volume ($V_L$) of the fluid through the first opening, wherein the fluid has an initial concentration ($C_i$) of the first gas and wherein a second volume ($V_C$) of the container is determined based on the initial concentration ($C_i$) of the first gas in the fluid, a target concentration ($C_f$) of the first gas in the fluid, a partition coefficient ($\varphi$) of the first gas, and the first volume ($V_L$), and configured to adjust pressure in the container at a predetermined pressure of the first gas to adjust the first gas concentration in the fluid to the target concentration ($C_f$), wherein the second volume ($V_C$) and the first volume ($V_L$) are correlated by:

$$V_C = \frac{V_L}{\phi}\left[\frac{M}{C_f V_L} + \frac{C_i}{C_f} - 1\right] + V_L$$

in that M is an amount of the first gas required to be introduced in the container to adjust the first gas concentration in the fluid to the target concentration ($C_f$).

In one embodiment, the device is configured to adjust concentration of the first gas in the fluid by adjusting the second volume ($V_C$). In another embodiment, the device is configured to adjust concentration of the first gas in the fluid for a predetermined value of the second volume ($V_C$) by adjusting the first volume ($V_L$). In a further embodiment, the container is provided with a second opening, the second opening is configured to adjust pressure in the container at the predetermined pressure with the first gas, wherein, the predetermined pressure is a partial pressure of the first gas and is determined by solubility parameter of the first gas. According to some embodiment, the device further comprises a third opening, the third opening is configured to dispense the fluid out of the container. According to some other embodiment, the device further comprises a seal configured to seal the container. According to a further embodiment, the device is provided with a jacket, the jacket providing thermal insulation to the container. According to yet another embodiment, the jacket is supplied with one or more of temperature control agents and the temperature control agents include one or more of dry ice, liquid nitrogen, chilled water, refrigerants, heat transfer fluids, compressed air, ice heating agents and electric coils. According to another embodiment, the predetermined pressure is a partial pressure of the first gas in a headspace of the container, wherein the headspace is volume of the container that is unoccupied by the fluid. According to yet a further embodiment, the container is provided with a second opening to adjust pressure in the container. In some other embodiments, the second opening is configured to introduce the amount (M) of the first gas in the container. In a further embodiment, the second opening is configured to educe the amount (M) of the first gas from the container. In one embodiment, the container is provided with a piston to adjust pressure in the container. In another embodiment, the piston is provided to adjust concentration of the first gas in the fluid by adjusting the second volume ($V_C$). In a further embodiment, the first opening is configured to adjust pressure in the container. In yet a further embodiment, the first opening is configured to introduce the amount (M) of the first gas in the container. In another embodiment, the first opening is configured to educe the amount (M) of the first gas from the container. In some other embodiments, the third opening is operable by an actuator. In some other embodiments, the first gas is selected from a group consisting of carbon dioxide, oxygen, air, argon, neon, xenon, helium, nitrogen, nitrous oxide, hydrocarbons, halocarbons, halohydrocarbons and a combination thereof. In another embodiment, the fluid is any one or more of beer, coffee, milk, cream, batter, dough, ice cream, wine, alcoholic beverage, cider, fruit juices and milkshake.

Now the subject matter shall be described with reference to the accompanying drawings.

BRIEF DESCRIPTION OF DRAWINGS

The subject matter shall now be described with reference to the accompanying figures, wherein.

DETAILED DESCRIPTION

Figure 1:
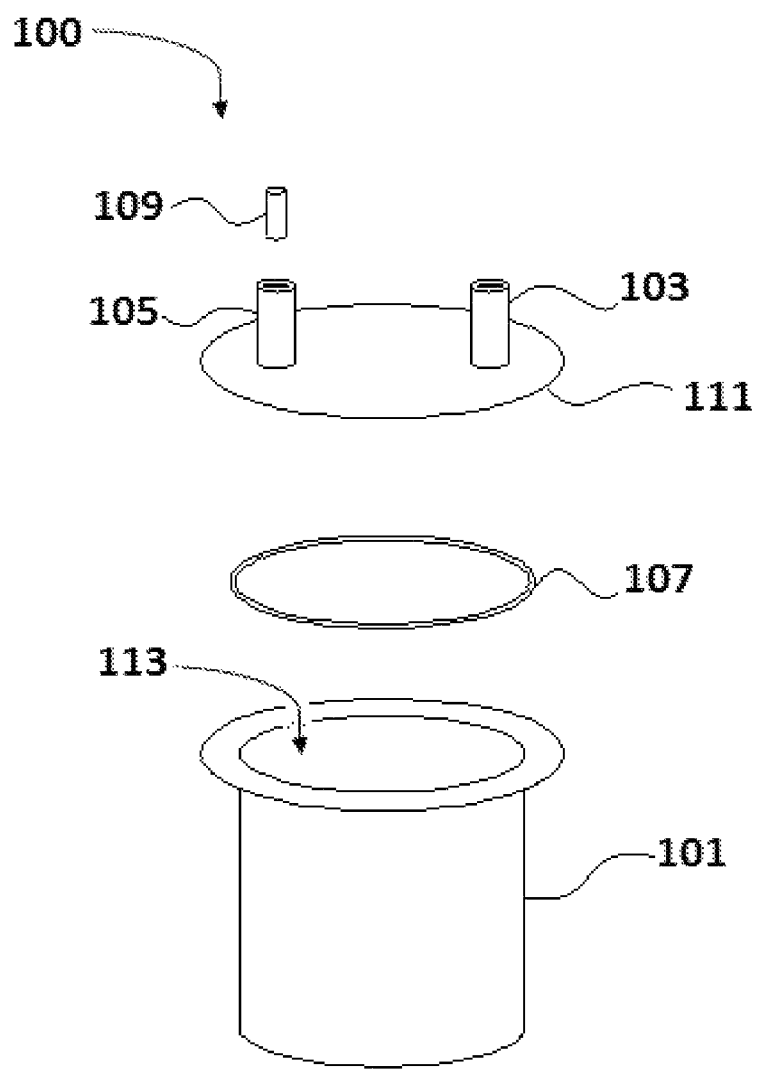
FIG. 1 is a schematic diagram according to one embodiment of the device of the present subject matter.

Before the present subject matter is described in further detail, it is to be understood that the subject matter is not limited to the particular embodiments described, and may vary as such. It is also to be understood that the terminology used herein is for the purpose of describing particular embodiments only, and is not intended to be limiting. It must be noted that as used herein, the singular forms "a", "an", and "the" include plural referents unless the context clearly dictates otherwise. Further, the following description uses beer and water as examples for describing the present subject matter. It shall become clear to a person skilled in the art, after reading this specification, that the present subject matter may be practiced for fluids other than beer or water, without regards to whether the fluids are edible or not.

Normally, beers contain a dissolved carbon dioxide level between 2.0 and 3.5 v/v depending on the beer style. At the end of fermentation, a carbon dioxide concentration level between 0.7 to 1.5 v/v is commonly seen. During finishing operations, additional carbon dioxide gas is injected into the beer, either directly into a flowing stream of beer or sparging a tank of beer. The final carbonation levels are tightly controlled to within 10% of the target depending on the beer style. However, achieving such level of control is not a simple matter. For example, a higher line back pressure or tank counter pressure can cause too much carbon dioxide dissolution. On the other hand, lower pressures or lower carbon dioxide injection rates can result in flat beer.

Producing nitrogenated beers, is significantly more complicated. Dissolved concentrations of both carbon dioxide and nitrogen should be tightly controlled. For optimal product quality, carbon dioxide concentration is targeted to a specific value within the range of 0.9 to 1.7 v/v and a nitrogen concentration is targeted to a specific value within the range of 0.015 v/v to 0.075 v/v. However, achieving such precisely controlled gas levels is extremely difficult because of the widely different solubility of nitrogen and carbon dioxide. Nitrogen or a mixture of nitrogen and carbon dioxide are injected directly into either a filled tank or a flowing stream of fermented beer containing about 1 v/v carbonation. The product quality is very variable because of the complexity involved with managing pressures, temperatures, composition of the injection gas, and the pressures at the receiving tanks. For example, too high a back pressure can cause too much carbon dioxide dissolution. Lower pressures or lower carbon dioxide content in the injected gas results in flat beer. Too much nitrogen injection can cause stripping of carbon dioxide from the beer. All the foam created during the process can result in stripping the beer of hops, bitterness, aroma or flavor, and foam-positive agents such as foam protein. The difficulties are compounded when nitrogen addition is required. The present subject matter provides a method and a device to ensure that the carbon dioxide and/or nitrogen concentration in a beer is adjusted to its desired level.

The present subject matter becomes of particular interest when it is desired to convert a normally carbonated beer produced by a brewery into a nitrogenated beer style at the point of dispense for serving. The present subject matter provides a solution that enables adjusting gas concentration in a beer without requiring highly sophisticated skills and precision equipment. In addition the present subject matter provides options for a lay person to exercise his creativity to create his own type of beer by adjusting gas concentration to suit his/her taste.

For example, the carbon dioxide concentration in a typical beer ranges between 2.0 and 3.5 v/v. However, in a nitrogenated beer, the concentration of carbon dioxide ranges between 0.9 to 1.7 v/v and nitrogen between 0.010 to 0.075 v/v. To convert a normal beer with carbon dioxide concentration 2.0-3.5 v/v, into a nitrogenated beer the carbon dioxide concentration must be reduced from 2.0-3.5 v/v to 0.9-1.7 v/v and nitrogen must be added. Removing a measured amount (or a close approximate) of carbon dioxide in controlled manner at the time of dispense is difficult. Similarly, adding a precise amount of nitrogen without upsetting the carbon dioxide balance is a significant challenge. The present subject matter provides solution to this problem.

According to one embodiment, the present subject matter provides a method and a device to adjust concentration of a first gas in a fluid by controlling a first volume of fluid ($V_L$) and a second volume ($V_C$) of a container. The fluid has an initial concentration ($C_i$) of the first gas. The objective is to adjust the concentration of the first gas to a target concentration ($C_f$). According to the present subject matter, the relationship between the first volume and the second volume and the initial concentration and final concentration may be expressed as follows:

$$\frac{V_C}{V_L} = \frac{1}{\phi}\left[\frac{M}{C_f V_L} + \frac{C_i}{C_f} - 1\right] + 1 \qquad \text{eq (1)}$$

Where $\varphi$ is a partition coefficient of the first gas in the fluid and M is an amount of the first gas that is added to the container for achieving the target concentration.

The partition coefficient $\varphi$ is related to the Henry's Law solubility parameter H for the gas-fluid pair (units atm/(v/v)) in the following manner:

$$\phi = \frac{HT^R}{p^R T}$$

wherein, T represents the absolute temperature of the fluid (units: K), and $T^R$ and $p^R$ are the absolute temperature and pressure conditions at which the gas volumes are referenced, typically 273 K and 1 atm. The dissolved concentration of the gas (C) is related to its existing partial pressure (p) under the conditions when the gas and the fluid are in thermodynamic equilibrium as defined by the Henry's Law solubility parameter H in the manner:

p=HC

The Henry's law solubility parameter is dependent on the nature of the gas-fluid pair, and the temperature. Therefore, partition function and the Henry's law solubility parameter could said to be related solubility parameters. Values of H in various units are available from published literature (for example, Perry's Chemical Engineers' Handbook 5$^{th}$ Edition (McGraw Hill) for many gases in water, and the American Society of Brewing Chemists for data for carbon dioxide-beer system). The solubility parameters for water and beer are similar. Generally, solubility of carbon dioxide in beer is smaller than solubility in water by about 10%.

The following discussion explains adjusting gas concentration in water according to the present subject matter. It shall become clear, after reading this specification, to a person skilled in the art that the procedure may be applied to beer or other fluids instead of water if the corresponding values of the partition coefficient and other parameters are substituted to practice the present method without departing from the basic concept of the present subject matter.

Equation (1) for carbon dioxide may be written as follows:

$$\frac{V_C}{V_L} = \frac{1}{\Phi_{CO2}}\left[\frac{M_{CO2}}{C_{fCO2} V_L} + \frac{C_{iCO2}}{C_{fCO2}} - 1\right] + 1 \qquad \text{eq (2)}$$

The subscript CO2 denotes the parameters as described for the equation (1) but associated with the carbon dioxide. The present example assumes that water at 38° F. with an initial carbon dioxide concentration 2.65 v/v needs to be adjusted to a target concentration of 1.25 v/v. Because the target concentration is lower than the initial concentration no additional gas needs to be added, i.e., $M_{CO2}$=0. The ratio of the initial concentration and target concentration is 2.12. The partition coefficient for the carbon dioxide in water at 38° F. is about 0.65 (for beer the partition coefficient is about 0.70). Upon appropriate adjustment for the unit conversions, substituting by these values in the equation (2), a linear relationship between the first and the second volume is obtained.

$$\frac{V_C}{V_L} = 2.72$$

That is, in a container having a volume 2.72 liters, pouring 1 liter of water having carbon dioxide concentration of 2.65 v/v and agitating the water and allowing the water to settle to achieve substantial equilibrium shall provide water with carbon dioxide at the target concentration 1.25 v/v. The remaining carbon dioxide is educed from the water and occupies volume of the container that is unoccupied (headspace) by the water. The final partial pressure of carbon dioxide may be determined by the equation p=HC. Thus partial pressure for the carbon dioxide turns out to be p=0.83 atm (H=0.66 atm/(v/v)). The product with the thus adjusted carbonation level may now be dispensed and served, or further processed using further adaptations as described below.

Now, that the carbon dioxide concentration in the water is adjusted to 1.25 v/v, the method may be further adapted to also adjust nitrogen concentration in the water to obtain desired nitrogen concentration. For the adjusting nitrogen concentration in the water the equation (1) may be written as follows:

$$\frac{V_C}{V_L} = \frac{1}{\Phi_{N2}}\left[\frac{M_{N2}}{C_{fN2} V_L} + \frac{C_2}{C_{fN2}} - 1\right] + 1 \qquad \text{eq (3)}$$

The subscript N2 denotes the parameters as described for the equation (1) but associated with the nitrogen. In the present case, the ratio of the first volume and the second volume is:

$$\frac{V_C}{V_L} = 2.72$$

Assuming that the initial concentration of the nitrogen in the water is zero then $C_{iN2}$=0. If a target concentration of nitrogen $C_{fN2}$=0.035 v/v is desired, considering that the partition coefficient of the nitrogen $\varphi_{N2}$=44.9, a value of $M_{N2}$=2.72×$V_L$ is required to be added. This addition may be achieved by charging the container to a nitrogen partial pressure of 1.59 atm, as determined by the equation p=HC with H=45.5 and C=0.035 v/v.

During this process, the container is never vented. Thus, the total pressure in the container is the sum of the partial pressures of carbon dioxide (0.83 atm) and nitrogen (1.59 atm), i.e., the total pressure at the end of the process is expected to be 2.42 atm abs.

It should be understood that when the process is performed in ambient air, a significant portion of $M_{N2}$ is provided from the ambient air rather than the injection port. A small amount of oxygen is also entrained in the process and exerts a corresponding partial pressure. The final total pressure could therefore be correspondingly slightly greater than the 2.42 atm value noted above.

It is also possible to add air instead of pure nitrogen. For example if it is desired to add $C_f$=0.040 v/v of air to the water at 1.25 v/v carbonation prepared as described above, an amount $M_{air}$=2.60×$V_L$ would be required to be added. When the method of the present subject matter is performed in ambient air, a portion of this total air requirement is provided by ambient air entrainment. Corresponding final air partial pressure would be 1.51 atm. The final total pressure would be $p_{CO2}+p_{air}$=0.83+1.51=2.34 atm abs.

Another example may illustrate the present subject matter in which the carbon dioxide concentration in water at 38° F. is increased. If the initial concentration of carbon dioxide in the water were zero, then equation (1) can be reduced accordingly using $C_i$=0. An amount of M for target concentration $C_f$=2.65 v/v may be determined based on the water volume ($V_L$), the container volume ($V_C$), and the partition coefficient ($\varphi_{CO2}$). The amount of carbon dioxide required to be injected $M_{CO2}$ would now depend on the container size because only a portion $M_{CO2}-(\varphi_{CO2} \cdot C_f(V_C-V)_L)$ of the total injected amount $M_{CO2}$ will dissolve in the water. For example, if the same container size as in the earlier examples $V_C$=2.72·$V_L$ is used, based on equation (2), a total amount of M=5.62 times $V_L$ is required to be introduced in the container. The corresponding final carbon dioxide partial pressure would be $p=HC_f$=(0.66)(2.65)=1.75 atm.

According to a further aspect of the present subject matter, the method is practiced in a temperature controlled environment. Generally, the subject matter may be practiced at the room temperature, however in some other cases, a jacket for controlling temperature may be provided along with the device of the present subject.

Following Table 1 shows examples of adjusting different gas concentrations in water at 38° F. according to the present subject matter. The partition coefficient and solubility data listed in this table are obtained from the Perry's Chemical Engineers' Handbook for water. As long as the ratio $V_C/V_L$ for the container and liquid volume are as listed and the initial and final gas compositions are adhered to, the final total pressure can be estimated by adding up all the partial pressures of the respective gases. To apply the teachings of the present subject matter to a fluid other than water, or for use with other gases than those listed, it is recommended that the H and φ values for the respective gases in the fluid of interest be used for a more accurate estimation, Although following table list only few gases. It shall become clear to a person skilled in the art, after reading this specification, that other similar method can be practiced with any gas other than those listed below as well as any fluid other than the water. A non-exhaustive list of gases includes methane, helium, argon, xenon, hydrogen, halocarbons, hydrocarbons, halohydrocarbons, etc. A non-exhaustive list of fluids includes coffee, cream, batter, dough, milkshake, ciders, fruit juice, alcoholic beverages, wines, ice cream etc.

TABLE 1

| Gas | Partition Coefficient, φ | Henry's Law Solubility Parameter, H, atm/(v/v) | Initial Conc., Ci, v/v | Target Conc., Cf, v/v | Gas added M, x$V_L$ at ref cond. | Final partial pressure, atm abs | Container Vol:LiqVol Vc/Vl | Description |
|---|---|---|---|---|---|---|---|---|
| CO2 | 0.65 | 0.66 | 2.65 | 1.25 | 0.00 | 0.83 | 2.72 | Decarbonation |
| CO2 | 0.65 | 0.66 | 0.00 | 2.65 | 5.62 | 1.75 | 2.72 | Carbonation |
| N2 | 44.90 | 45.50 | 0.00 | 0.035 | 2.74 | 1.59 | 2.72 | Nitrogenation |
| O2 | 21.80 | 22.04 | 0.00 | 0.019 | 0.74 | 0.42 | 2.72 | Oxygen addition, Low Level |
| O2 | 21.80 | 22.04 | 0.00 | 0.035 | 1.35 | 0.77 | 2.72 | Oxygen addition, High Level |
| Air | 37.20 | 37.70 | 0.00 | 0.040 | 2.60 | 1.51 | 2.72 | Aeration |
| Ar | 25.10 | 25.40 | 0.00 | 0.035 | 1.55 | 0.89 | 2.72 | Argon addition |
| He | 101.33 | 102.57 | 0.00 | 0.035 | 6.15 | 3.59 | 2.72 | Helium addition |
| H2 | 47.46 | 48.04 | 0.00 | 0.035 | 2.90 | 1.68 | 2.72 | Hydrogen addition |

The present subject matter further provides a device to adjust gas concentrations in a fluid. A schematic diagram according to one embodiment of the device 100 of the present subject matter is shown in FIG. 1. The device 100 comprises a container 101. The container 101 has a lid 111, a seal 107, a first opening 113, a second opening 105, a third opening 103. Although the second opening 105 and the third opening 103 are shown located on the lid 111, they may be located at any suitably convenient location, for example, on container 101. The seal 107 is sandwiched between the container 101 and the lid 111. The seal 107 in this embodiment shown to be an O-ring, however should become clear to a person skilled in the art, after reading this specification, that the device 100 may have any other sealing mechanism that renders the device 100 substantially leak-tight. In one embodiment the seal 107 is a gasket and is provided to close the container 101 with lid 111 to reduce leakage of the contents of the device 100 to the outside environment. The first opening 113 is configured to receive a first volume ($V_L$) of a fluid in the container 101. In one embodiment, any one of the third opening 103 and the second opening 105 may be used for injecting the fluid into the container 101. In some other embodiments the lid 111 may be openable. In some embodiments, the first opening 113 and/or the second opening 105 and/or the third opening 103 may have arrangements for enabling one way flow of the fluids from or out of the container 101. The first opening 113, second opening 105 and/or the third opening 103 may include valves to enable filling or venting the contents of container 101. In some embodiments, the valves may be built-in, automatic shut-off valves that can be forced open for filling or venting when a fitting is inserted. One such fitting 109 is shown in the FIG. 1. A person skilled in the art shall appreciate, after reading this specification, that any suitable valve mechanism may be used to shut off medium exchange from the container 101 to the outside. Fitting 109 may be optionally connected with external tubing to transport the fluid or gas between the device 100 and external equipment. The device 100 may also include a pressure gauge (not shown) to read the internal pressure. In some embodiments, the second opening 105 of the device 100 may be configured to pressurize the container 101 at a predetermined pressure with the first gas, to introduce an amount (M) of the first gas in the container 101. The predetermined pressure is determined based on the solubility of the first gas in the fluid. In some embodiments, the predetermined pressure is partial pressure of the first gas. According to another aspect of the present subject matter the device 100 may be suspended in a temperature controlled environment. In one possibility, the device 100 may be suspended in a jacket for providing a temperature controlled environment and the jacket may include one or more temperature controlling agents, such as ice, dry ice, liquid nitrogen, chilled water, refrigerants, heat transfer fluids, compressed air, ice or other heating or cooling agents or mechanism such as electric coils for heating to gas coils for cooling. The device 100 may be provided with other options for safety, such as safety valve etc. The device 100 may also be configured with a handle for convenience.

In one embodiment, the device 100 is designed for adjusting gas concentration of in a one liter of beer having initial carbon dioxide concentration of 2.65 v/v. The partition coefficient for carbon dioxide in beer is about 0.7. If the volume of the container 101 is 2.72 liter, dispensing the beer according in the device 100 and following the steps of the method according to the present subject matter shall result in a beer having carbon dioxide concentration 1.20 v/v. The beer may be then further processed for nitrogenation or further adjusting carbonation according to the method of present subject matter by pressurizing the container 101 with an amount (M) as explained in the aforementioned description. Similarly, for obtaining a target concentration of 0.65 v/v carbon dioxide in the beer from initial concentration 2.65 v/v, half a liter of the beer may be dispensed in the container 101. The nitrogenation or further carbonation of the beer may follow as explained earlier.

Figure 2:
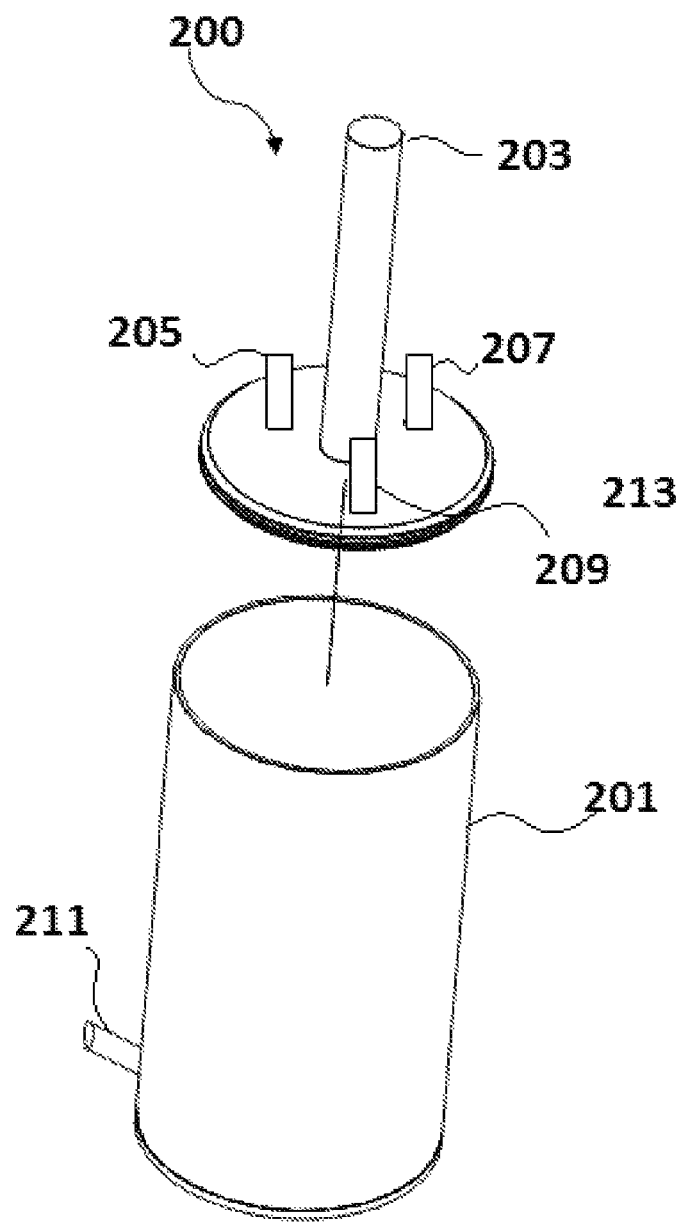
FIG. 2 shows a schematic diagram according another embodiment of the device of the present subject matter.

FIG. 2 shows a schematic diagram according another embodiment of the device 200 of the present subject matter. The device 200 is provided with a container 201. The device 200 is further provided with a piston 203. The piston 203 may be used for controlling the volume of the container 201. Controlling volume of the container 201 ensures that a user may apply his or her creativity to adjust concentration of the gases in the fluid according to his or her choice. The device 200 is provided with a first opening 205, a second opening 207 and a third opening 211. The first opening 205, the second opening 207 may in applied to dispense the fluid or the gases in the container 201, whereas the third opening 211 may be used for dispensing the fluid out of the container 201. An optional pressure sensor or a gage 209 may be used to read the internal pressure of device 200. Although the first openings 205 and the second opening 207, and the pressure gage 209 are located on the piston 203 in FIG. 2, they may be located at any other suitable site, including on the container 201. The first openings 205, the second opening 207, and opening 211 may also be used in conjunction with appropriate valves that allow or obstruct flow of fluid and gas into or out of the device 200.

Figure 3:
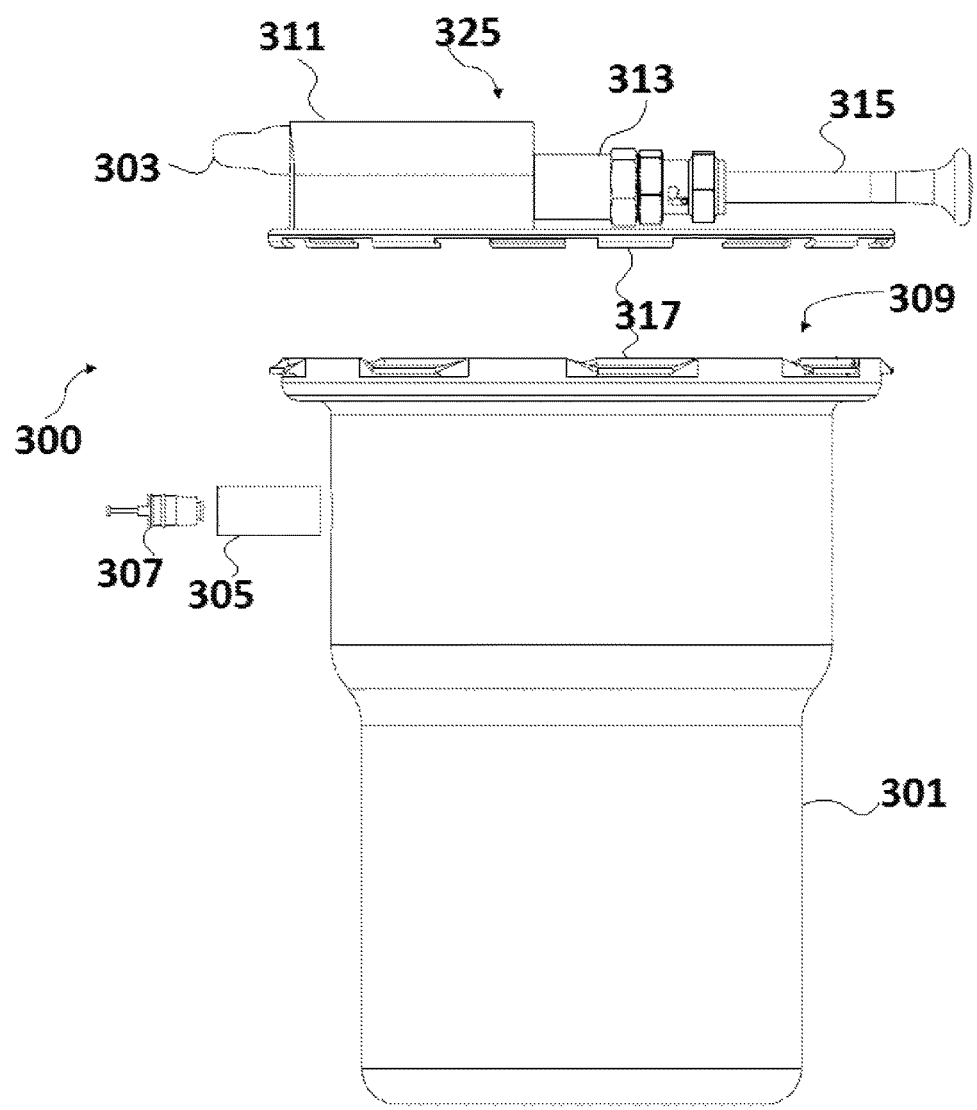
FIG. 3 shows a schematic diagram according yet another embodiment of the device of the present subject matter.

FIG. 3 shows a schematic diagram according yet another embodiment of the device 300 of the present subject matter. The device 300 comprises a container 301. The container 301 is configured to have a first opening 309 to receive the fluid. Lid assembly 325 is sealingly applied to the container 301 to close and seal the first opening 309. Any suitable mechanism to secure the lid assembly 325 to the container 301 may be employed. In one embodiment, the lid assembly 325 seals the container 301 when applied and turned with respect to the axis of the container 301. Turning the lid assembly 325 engages clamps 317 provided with the lid assembly 325 and the container 301 and prevents the lid assembly 325 from separating from the container 301. In some embodiments, the cams 317 are designed so that, less than a full turn is required to completely seal the container when pressurized. An optional sealing member may be provided to form a leak-tight seal between the container 301 and the lid assembly 325. A second opening 305 is also provided for device 300 to allow for pressurizing the device with the gas. The second opening 305 may be provided with an optional built-in automatic shut-off valve 307. The valve 307 may be forced open by inserting a mating fitting into the opening 305. In some embodiments, the valve 307 is a Schrader valve. In some embodiments, the device 300 is configured with an overpressure relief mechanism for safety. In some other embodiments, a lid-locking mechanism may also be provided that prevents the lid assembly 325 from being separated from the container 301 when the device 300 is pressurized. The lid assembly 325 includes a valve block 311, an actuator valve block 313, an actuator 315, and a fluid dispense nozzle or a third opening 303. By applying pressure on the actuator 315, a dispense valve within the valve block 313 opens, allowing for fluid to be discharged from the container 301 through the dispense nozzle 303 into a receiver or a serving container. In some embodiments, the device 300 may be provided with a handle to allow for ease and convenience of use. In some other embodiments, the device 300 is tilted to dispense contains from the dispense nozzle 303.

Figure 4:
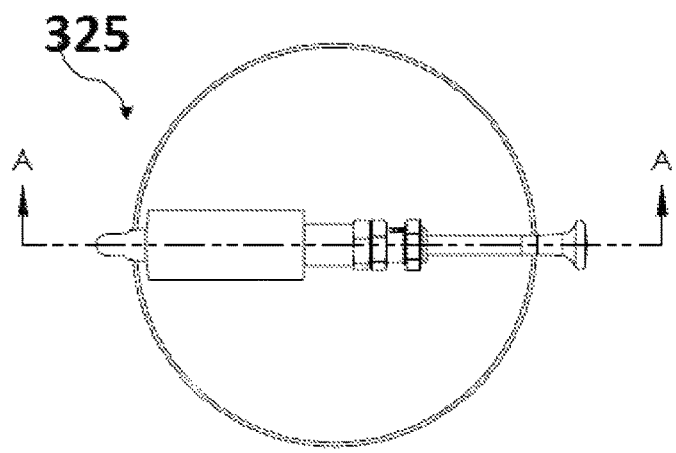
FIG. 4 and FIG. 5 show more details of the schematic diagram according to the yet another embodiment of the present subject matter.
Figure 5:
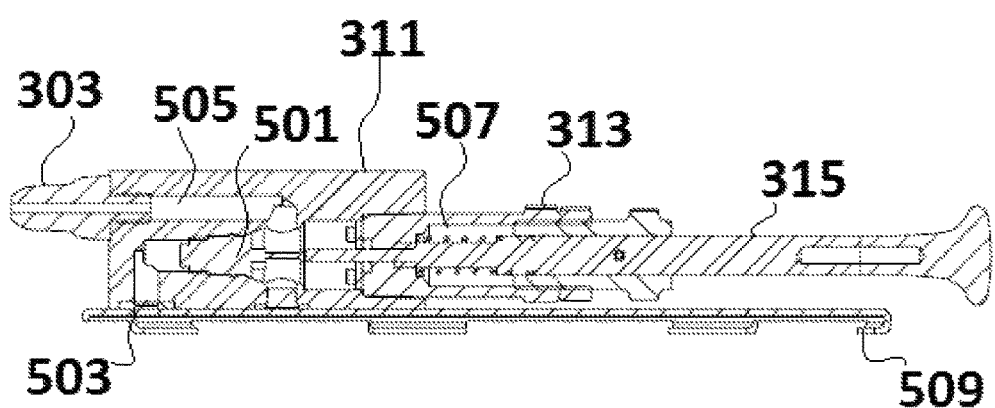

FIG. 4 and FIG. 5 show more details of the schematic diagram according to the yet another embodiment of the present subject matter. FIG. 4 is a top view of the lid assembly 325 of device 300 shown in FIG. 3 and FIG. 5 is a cross-sectional view of the lid assembly 325 as sectioned by cutting plane AA in FIG. 4. The lid assembly 325 constitutes the actuator 315, the actuator block 313, the valve block 311, and the dispense nozzle 303. When pressure is applied, for example, thumb pressure at the end of the actuator 315, is slides through the actuator block 313 and activates and opens the dispense valve 501. When valve 501 opens, a flow path for the contents in the container is created through the opening 503 in the lid via channel 505 to the dispense nozzle 303. It may be required in some embodiments to tilt the device 300 for dispensing the fluid. An optional return spring 507 configured in the actuator block 313 returns the actuator 315 to the original position when the thumb pressure is reduced or removed, slowing the dispense rate or shutting off the dispense altogether.

While the subject matter may be susceptible to various modifications and alternative forms, specific embodiments have been shown by way of example in the drawings and have been described herein. Alternate embodiments or modifications may be practiced without departing from the spirit of the present subject matter. The drawings shown are schematic drawings and may not be to the scale. While the drawings show some features of the subject matter, some features may be omitted. Alternatively, in some other cases some features may be emphasized while others are not. Further, the methods disclosed herein may be performed in manner and/or order in which the methods are explained. Alternatively, the methods may be performed in manner or order different than what is explained without departing from the spirit of the present subject matter. It should be understood that the subject matter is not intended to be limited to the particular forms disclosed. Rather, the subject matter is to cover all modifications, equivalents, and alternatives falling within the spirit and scope of the subject matter as defined by the following appended claims.

What is claimed is:

1. A device to adjust concentration of a first gas in a fluid to a target concentration ($C_f$) comprising:
a container, the container comprises a first opening, the container is configured to receive a first volume ($V_L$) of the fluid through the first opening, wherein the fluid has an initial concentration ($C_i$) of the first gas and wherein a second volume ($V_C$) of the container is determined based on the initial concentration ($C_i$) of the first gas in the fluid, a target concentration ($C_f$) of the first gas in the fluid, a partition coefficient ($\varphi$) of the first gas, and the first volume ($V_L$), and configured to adjust pressure in the container at a predetermined pressure of the first gas to adjust the first gas concentration in the fluid to the target concentration ($C_f$)
wherein the second volume ($V_C$) and the first volume ($V_L$) are correlated by:

$$V_C = \frac{V_L}{\varphi}\left[\frac{M}{C_f V_L} + \frac{C_i}{C_f} - 1\right] + V_L$$

in that M is an amount of the first gas required to be introduced in the container to adjust the first gas concentration in the fluid to the target concentration ($C_f$).

2. The device of claim 1, wherein the device is configured to adjust concentration of the first gas in the fluid by adjusting the second volume ($V_C$).

3. The device of claim 1, wherein the device is configured to adjust concentration of the first gas in the fluid for a predetermined value of the second volume ($V_C$) by adjusting the first volume ($V_L$).

4. The device of claim 1, wherein the container is provided with a second opening, the second opening is configured to adjust pressure in the container at the predetermined pressure with the first gas, wherein, the predetermined pressure is a partial pressure of the first gas and is determined by solubility parameter of the first gas.

5. The device of claim 1, wherein the device further comprises a third opening, the third opening is configured to dispense the fluid out of the container.

6. The device of claim 1, wherein, the device further comprises a seal configured to seal the container.

7. The device of claim 1, wherein the device is provided with a jacket, the jacket providing thermal insulation to the container.

8. The device of claim 7 wherein, the jacket is supplied with one or more of temperature control agents and the temperature control agents include one or more of dry ice, liquid nitrogen, chilled water, refrigerants, heat transfer fluids, compressed air, ice heating agents and electric coils.

9. The device of claim 1, wherein the predetermined pressure is a partial pressure of the first gas in a headspace of the container, wherein the headspace is volume of the container that is unoccupied by the fluid.

10. The device of claim 1, wherein the container is provided with a second opening to introduce the amount (M) of the first gas in the container.

11. The device of claim 1 wherein the container is configured to educe the first gas from the fluid.

12. The device of claim 1, wherein the container is provided with a piston to adjust pressure in the container.

13. The device of claim 12, wherein the piston is provided to adjust concentration of the first gas in the fluid by adjusting the second volume ($V_C$).

14. The device of claim 1, wherein the first opening is configured to adjust pressure in the container.

15. The device of claim 14, wherein the first opening is configured to introduce the amount (M) of the first gas in the container.

16. The device of claim 14 wherein the first opening is configured to educe the first gas from the fluid.

17. The device of claim 5, wherein the third opening is operable by an actuator.

18. The device of claim 1, wherein the first gas is selected from a group consisting of carbon dioxide, oxygen, air, argon, neon, xenon, helium, nitrogen, nitrous oxide, hydrocarbons, halocarbons, halohydrocarbons and a combination thereof.

19. The device of claim 1, wherein the fluid is any one or more of beer, coffee, milk, cream, batter, dough, ice cream, wine, alcoholic beverage, cider, fruit juices and milkshake.

20. The device of claim 1, further comprises a handle attached to the container.

* * * * *